(12) United States Patent
Tuseth et al.

(10) Patent No.: US 10,893,847 B2
(45) Date of Patent: Jan. 19, 2021

(54) TRANSCATHETER INSERTION SYSTEM

(71) Applicant: NUHEART AS, Bergen (NO)

(72) Inventors: Vegard Tuseth, Bergen (NO); Matthew Keillor, Inver Grove Heights, MN (US); Philip J. Haarstad, Chanhassen, MN (US); Shawn Patterson, Bergen (NO); Steve Schmidt, Blaine, MN (US); Dan Burrow, Milaca, MN (US)

(73) Assignee: NUHEART AS, Bergen (NO)

( * ) Notice: Subject to any disclaimer, the term of this patent is extended or adjusted under 35 U.S.C. 154(b) by 2 days.

(21) Appl. No.: 14/984,998

(22) Filed: Dec. 30, 2015

(65) Prior Publication Data

US 2017/0189650 A1    Jul. 6, 2017

(51) Int. Cl.
| | | |
|---|---|---|
| *A61B 8/08* | (2006.01) | |
| *A61M 1/10* | (2006.01) | |
| *A61M 1/12* | (2006.01) | |
| *A61B 6/00* | (2006.01) | |
| *A61B 6/12* | (2006.01) | |

(52) U.S. Cl.
CPC ........... *A61B 8/0841* (2013.01); *A61M 1/101* (2013.01); *A61M 1/125* (2014.02); *A61B 6/12* (2013.01); *A61B 6/487* (2013.01); *A61B 8/0883* (2013.01)

(58) Field of Classification Search
CPC ...... A61M 25/0662; A61M 2025/0681; A61M 25/01; A61M 25/0105; A61M 25/0108; A61M 2025/0175; A61M 25/10; A61M 25/1009; A61M 25/1006; A61M 25/1036; A61M 29/00; A61M 29/02; A61M 2029/025; A61F 2/962; A61F 2/966
See application file for complete search history.

(56) References Cited

U.S. PATENT DOCUMENTS

| | | |
|---|---|---|
| 5,571,215 A | 11/1996 | Sterman et al. |
| 5,728,122 A | 3/1998 | Leschinsky et al. |
| 5,921,913 A | 7/1999 | Siess |
| 6,134,467 A | 10/2000 | Ouchi |
| 6,196,230 B1 | 3/2001 | Hall et al. |
| 6,425,916 B1 | 7/2002 | Garrison et al. |
| 7,295,878 B1 | 11/2007 | Meadows et al. |
| 7,878,967 B1 | 2/2011 | Khanal |
| 7,942,804 B2 | 5/2011 | Khaw |
| 8,157,852 B2 | 4/2012 | Bloom et al. |

(Continued)

FOREIGN PATENT DOCUMENTS

| | | |
|---|---|---|
| AU | 2014201432 A1 | 10/2014 |
| EP | 1 907 028 A1 | 4/2008 |

(Continued)

OTHER PUBLICATIONS

Merriam-Webster definition for "integral" accessed Nov. 20, 2019; https://www.merriam-webster.com/dictionary/integral.*

*Primary Examiner* — Wade Miles
(74) *Attorney, Agent, or Firm* — BakerHostetler (57) ABSTRACT

A transcatheter insertion system is provided for the insertion of an intracorporeal device using an insertion device. The system comprises an outer sheath arranged and configured to form a passageway for the intracorporeal device and/or the insertion device. The outer sheath guides the insertion device. A method of transcatheter insertion with the system is also provided.

60 Claims, 5 Drawing Sheets

(56) References Cited

U.S. PATENT DOCUMENTS

| | | |
|---|---|---|
| 8,738,147 B2 | 5/2014 | Hastings et al. |
| 9,314,556 B2 | 4/2016 | Tuseth |
| 9,539,378 B2 | 1/2017 | Tuseth |
| 10,130,742 B2 | 11/2018 | Tuseth |
| 2001/0047150 A1 | 11/2001 | Chobotov |
| 2002/0082584 A1* | 6/2002 | Rosenman ........ A61M 25/0014 604/523 |
| 2002/0099396 A1 | 7/2002 | Slaker et al. |
| 2002/0173742 A1 | 11/2002 | Keren et al. |
| 2002/0173817 A1* | 11/2002 | Kletschka ........ A61B 17/22032 606/194 |
| 2003/0100920 A1 | 5/2003 | Akin et al. |
| 2003/0181843 A1 | 9/2003 | Bibber et al. |
| 2003/0233143 A1 | 12/2003 | Gharib et al. |
| 2004/0006305 A1* | 1/2004 | Hebert .............. A61M 25/0021 604/96.01 |
| 2004/0097973 A1 | 5/2004 | Loshakove et al. |
| 2004/0098081 A1* | 5/2004 | Landreville .............. A61F 2/91 623/1.11 |
| 2004/0236170 A1 | 11/2004 | Kim |
| 2004/0243051 A1 | 12/2004 | Monzyk et al. |
| 2005/0075696 A1 | 4/2005 | Forsberg et al. |
| 2005/0165344 A1 | 7/2005 | Dobak, III |
| 2005/0187425 A1 | 8/2005 | Alferness et al. |
| 2006/0079736 A1 | 4/2006 | Chin |
| 2006/0089707 A1 | 4/2006 | Vassiliades et al. |
| 2006/0155158 A1 | 7/2006 | Aboul-Hosn |
| 2007/0249985 A1 | 10/2007 | Brenneman et al. |
| 2008/0195226 A1* | 8/2008 | Williams ................... A61F 2/04 623/23.67 |
| 2008/0300574 A1 | 12/2008 | Belson et al. |
| 2009/0088597 A1 | 4/2009 | Frazier et al. |
| 2009/0093670 A1 | 4/2009 | Annest et al. |
| 2009/0093751 A1 | 4/2009 | Tao et al. |
| 2009/0105654 A1 | 4/2009 | Kurth et al. |
| 2009/0182188 A1 | 7/2009 | Marseille et al. |
| 2009/0228078 A1 | 9/2009 | Zhang et al. |
| 2010/0191035 A1 | 7/2010 | Kang et al. |
| 2010/0268316 A1 | 10/2010 | Brenneman et al. |
| 2010/0331972 A1 | 12/2010 | Pintor et al. |
| 2011/0130619 A1 | 6/2011 | Whisenant et al. |
| 2011/0184224 A1 | 7/2011 | Garrigue |
| 2011/0196190 A1 | 8/2011 | Farnan et al. |
| 2011/0234155 A1 | 9/2011 | Chen et al. |
| 2011/0257723 A1 | 10/2011 | McNamara |
| 2011/0276075 A1 | 11/2011 | Fung et al. |
| 2011/0306916 A1 | 12/2011 | Nitzan et al. |
| 2012/0053657 A1 | 3/2012 | Parker et al. |
| 2012/0059459 A1 | 3/2012 | Asirvatham et al. |
| 2012/0139355 A1 | 6/2012 | Ganem et al. |
| 2012/0146575 A1 | 6/2012 | Armstrong et al. |
| 2012/0150259 A1 | 6/2012 | Meskens |
| 2012/0165928 A1 | 6/2012 | Nitzan et al. |
| 2012/0172654 A1 | 7/2012 | Bates |
| 2012/0172655 A1 | 7/2012 | Campbell et al. |
| 2012/0178985 A1 | 7/2012 | Walters et al. |
| 2012/0232316 A1 | 9/2012 | Nappa |
| 2012/0245649 A1 | 9/2012 | Bohori et al. |
| 2012/0259263 A1 | 10/2012 | Celermajer et al. |
| 2012/0265003 A1 | 10/2012 | Dambrosio et al. |
| 2012/0301318 A1 | 11/2012 | Er |
| 2013/0060267 A1 | 3/2013 | Farnan et al. |
| 2013/0127253 A1 | 5/2013 | Stark et al. |
| 2013/0193914 A1 | 8/2013 | Gaddam et al. |
| 2013/0301318 A1 | 11/2013 | Asako et al. |
| 2014/0005466 A1 | 1/2014 | Crosby et al. |
| 2014/0031607 A1 | 1/2014 | Zilbershlag et al. |
| 2014/0236123 A1 | 8/2014 | Birmingham et al. |
| 2014/0287274 A1 | 9/2014 | Hwang |
| 2014/0336445 A1 | 11/2014 | Farnan et al. |
| 2015/0005570 A1 | 1/2015 | Fritz et al. |
| 2015/0119633 A1 | 4/2015 | Haselby et al. |
| 2015/0223839 A1 | 8/2015 | Spence et al. |
| 2015/0250935 A1 | 9/2015 | Anderson et al. |
| 2015/0258260 A1 | 9/2015 | Tuseth |
| 2015/0258312 A1 | 9/2015 | Tuseth |
| 2015/0335801 A1 | 11/2015 | Farnan et al. |
| 2016/0022896 A1 | 1/2016 | Burkhoff et al. |
| 2016/0175501 A1 | 6/2016 | Schuermann |
| 2017/0000935 A1 | 1/2017 | Vasilyev et al. |
| 2017/0043077 A1 | 2/2017 | Tuseth et al. |
| 2017/0047762 A1 | 2/2017 | Tuseth et al. |
| 2017/0106176 A1 | 4/2017 | Taft et al. |
| 2017/0216029 A1 | 8/2017 | Crowley et al. |

FOREIGN PATENT DOCUMENTS

| | | |
|---|---|---|
| EP | 2338540 A1 | 6/2011 |
| GB | 2504176 A | 1/2014 |
| JP | 2008-545083 A | 12/2008 |
| JP | 2012-523894 A | 10/2012 |
| WO | WO199727898 A1 | 8/1997 |
| WO | 2000027312 | 5/2000 |
| WO | 2001078580 | 10/2001 |
| WO | 2005/037345 A2 | 4/2005 |
| WO | 2007/003351 A1 | 1/2007 |
| WO | 2007003351 A1 | 1/2007 |
| WO | 2008027869 A2 | 3/2008 |
| WO | 2008055301 A1 | 5/2008 |
| WO | WO2008106717 A1 | 9/2008 |
| WO | WO2008134267 A2 | 11/2008 |
| WO | WO2009134471 A1 | 11/2009 |
| WO | WO2010042056 A1 | 4/2010 |
| WO | WO2010114666 A1 | 10/2010 |
| WO | 2010/132451 A2 | 11/2010 |
| WO | WO2011011787 A2 | 1/2011 |
| WO | 2013036588 A1 | 3/2013 |
| WO | 2013/096965 A1 | 6/2013 |
| WO | 2015075576 A1 | 5/2015 |
| WO | 2015/140179 A1 | 9/2015 |
| WO | WO2015140179 A2 | 9/2015 |

* cited by examiner

TRANSCATHETER INSERTION SYSTEM

The present invention generally relates to the field of medical devices and surgery devices. More specifically, the invention relates to a catheter and corresponding methods of use of the catheter. The present invention is particularly useful in the context of minimally invasive transcatheter and/or percutaneous procedures, such as those described in PCT Application No. PCT/EP2015/055578, entitled "PERCUTANEOUS SYSTEM, DEVICES AND METHODS" filed 17 Mar. 2015, and published as WO 2015/140179 A2, and expressly incorporated herein by reference in its entirety.

FIELD OF THE INVENTION

Background

Examples of mechanical circulatory support systems (MCS) include ventricular assist devices (VADs). A VAD is a mechanical pumping device capable of supporting heart function and blood flow. Specifically, a VAD helps one or both ventricles of the heart to pump blood through the circulatory system. Left ventricular assist devices (LVAD), right ventricular assist devices (RVAD) and biventricular assist devices (BiVAD) are currently available. Also, circulatory support systems may include cardiopulmonary support (CPS, ECMO), which provide means for blood oxygenation as well as blood pumping. Such devices may be required during, before and/or after heart surgery or to treat severe heart conditions such as heart failure, cardiopulmonary arrest (CPA), ventricular arrhythmia or cardiogenic shock.

Traditionally, VADs are fitted during open-heart surgery through an incision in the chest and the procedure involves puncturing the apex of the left ventricle to re-route blood from the ventricle to the aorta through an external pump. An example of a device used in a surgical VAD is HeartMate II™. Such surgical procedures are clearly invasive and unsuitable for weaker and vulnerable patients as they involve a greater recovery time and carry the risks of infection and trauma. This is particularly the case in the treatment of children for whom existing surgical equipment and devices are comparatively bulkier and more invasive, and a reduction of the size of the equipment is often difficult if not impossible in view of the equipment and procedure involved. Furthermore, these devices require the intervention from a team of skilled surgical staff in a hospital environment and are therefore less available and costly.

More recent procedures are non-surgical and involve the insertion of a VAD through a small incision made at the groin of the patient. A popular version of such so-called percutaneous VAD is the TandemHeart™ device. A tube is introduced through an incision adjacent the groin of the patient and advanced along the femoral vein and inferior vena cava, across the intra-atrial septum and into the left atrium so that oxygenated blood from the left atrium is fed into a pumping device located outside the patient's body and recirculated through an outflow tube into the femoral artery. Although this device has shown promising results, it only provides short-term support (up to two weeks) and is unsuitable for long-term treatments. The external pump is bulky and requires the patient's immobilization for as long as the device is fitted. Furthermore, there is a risk of life-threatening infection around the groin incision, which remains open during the treatment, and of considerable bleeding from a major artery. In addition, the tube of the TandemHeart™ ends in the left atrium from which blood is pumped out and led outside the patient's body. This type of blood inlet system can potentially become hindered, if not blocked, if surrounding tissues are accidentally sucked in, thereby resulting in a loss of efficiency.

Another popular percutaneous VAD is the Impella™ device, which is inserted into the femoral artery and descending aorta. The Impella™ device comprises an elongated end, which is implanted across the natural aortic valve, with a blood inlet placed in the left ventricle and a blood outlet above the aortic valve. A pump circulates blood from the inlet to the outlet. The driveline is externalised through the femoral artery during use and the same limitations apply as with TandemHeart™ and other current percutaneous MCS systems. This device is approved to provide support for up to a week. There is therefore a need for a device with reduced risk of infection and bleeding and increased mechanical stability which can be used as part of a short-term "bridge to recovery" treatment or as a long-term treatment including patient mobilisation. In addition, the efficiency of the pump is limited because it is not possible to insert a pump of the size required to provide a suitable blood flow using percutaneous arterial access. Presently, the problem of limited pump capacity and duration with percutaneous MCS is solved either by inserting larger intracorporeal pumps surgically or by choosing an extracorporeal pump, with all the potential problems as described above.

Known mechanical circulatory support systems are life-saving. However, they remain costly, complex and have limited clinical potential with a majority of patients still passing away unaided.

Currently available percutaneous treatments rely on the main structures of the patient's anatomical vascular structure to be undamaged. However, many heart patients are children with congenital heart defects or elderly patients often with anatomical and vascular anomalies, such as calcifications and valvular disease. With surgery, such limitations may be overcome but benefit is hampered by the risk associated with surgical trauma. There is therefore a need for a procedure and device that can safely and predictably be deployed by percutaneously achieving access from one anatomical structure to another as this will allow for safe delivery of more efficient pumps without surgical trauma.

Most known systems for insertion of intracorporeal devices involve the use of separate instruments for each step of the procedure. The use of separate instruments means that the user needs to insert/or and remove each separate instrument during each step of the procedure, resulting in a significant amount of manipulation which increases the risk of discomfort and injury to the patient. In practice, there is also a need to facilitate the accurate movement and guiding of the system during insertion of an intracorporeal device. In particular, there is a need to provide a system that is more forgiving for example of uncontrolled movements that may be made by an operator when manipulating the system, wherein such movements may result in injury to the patient. The operator needs to be able to control the procedure proximally so that his movements translate into smaller, more accurate and precise movements of the device.

It is an object of this invention to mitigate problems such as those described above.

SUMMARY OF THE INVENTION

According to a first aspect, there is provided a transcatheter insertion system for the insertion of an intracorporeal device using an insertion device, wherein the system comprises an outer sheath arranged and configured to form a passageway for the intracorporeal device and/or the insertion device and said outer sheath comprises means for guiding the insertion device.

Advantageously, the guiding means facilitates the accurate movement and guiding of the system during insertion of the intracorporeal device into a patient, thus improving safety and minimising the risk of injury to the patient.

It is preferred that the guiding means is positioned adjacent to or at a distal end of the outer sheath. Typically, the distal end of the outer sheath is the operational site of the system, i.e. the site where manipulation of the position of the insertion device occurs. Advantageously, providing the guiding means adjacent to or at the distal end of the outer sheath therefore allows for accurate and precise control of the position and movement of the insertion device during insertion into a patient.

Preferably, the guiding means is substantially ring-shaped. Other shapes are envisaged within the context of this invention, for example, the guiding means may have a shape such as square, rectangular, hexagonal, oval, and the like, depending on specific requirements. However, it has been found that the provision of a ring shape enables the most control over movement of the insertion device when inserted into a patient. It is preferred that the guiding means has a doughnut shape. Provision of a guiding means having a doughnut shape is advantageous since it enables accurate and precise guiding of the insertion device as it is inserted into an anatomical compartment of a patient. Additionally, the doughnut shape of the guiding means improves the ease in which the insertion device may be inserted and move within the outer sheath of the system (particularly in the embodiment wherein the outer sheath is cylindrical), resulting in less trauma to a patient. Preferably, the guiding means has an outer diameter such that it fits inside the inner diameter of the outer sheath. Advantageously, this allows the guiding means to be held securely within the outer sheath, minimising the risk that it becomes detached therefrom. Preferably, the guiding means is integrally formed or non detachable from the outer sheath.

The guiding means preferably narrows the distal opening of the outer sheath. In other words, the guiding means, which may or may not be integrally formed with the sheath, preferably comprises an opening which is narrower than the distal opening of the sheath. Preferably, the opening of the guiding means is coaxially aligned with the longitudinal axis of the sheath.

It is preferred that the inner dimensions of the guiding means are smaller than the inner dimensions of the outer sheath. Preferably, the inner diameter of the guiding means is smaller than the inner diameter of the outer sheath (for example, in the embodiment wherein the guiding means has a doughnut shape). The smaller dimensions of the guiding means has the effect of narrowing the exit from the outer sheath, such that the insertion device will be guided out of the outer sheath substantially along or close to the central axis of the outer sheath. Advantageously, the provision of a narrower exit from the outer sheath allows the system to be more forgiving of the operator's manipulation, where the operator's movements translate into smaller movements of the insertion device which allow for improved accuracy and precision during insertion. Thus, the guiding means allows the system to be more forgiving of uncontrolled manipulations by the user which may otherwise result in injury or discomfort to the patient.

In one embodiment, the guiding means may comprise a substantially rigid material. It will be understood that the term substantially rigid material means a material that will not change shape during insertion. Typically, a substantially rigid material may be a biocompatible polymer, a metal such as stainless steel, etc. In another embodiment, the guiding means may comprise an inflatable balloon. Preferably, the inflatable balloon may comprise a biocompatible polymer.

Preferably, the guiding means comprises a detection and/or visualisation means. Preferably, the detection and/or visualisation means comprises a marker. Preferably, the guiding means comprises a material visible by means of any one of X-ray, fluoroscopy, echocardiography and/or ultrasound techniques. The present invention can therefore allow a precise visualisation of the longitudinal and/or axial location and positioning of the sheath, as well that the depth of potential puncture points.

In one embodiment, that marker may be provided as a band on the guiding means. In one embodiment, the marker may comprise a metallic material which may be detected by a user during insertion of the device. Advantageously, the provision of a detection and/or visualisation means allows the operator to determine the position of the system during insertion, such that the user can adjust and control the position of the system to ensure that the system travels along the required path and does not accidentally perforate any veins or anatomical walls which may lead to injury.

Typically, the insertion device comprises one or more of a guide wire, a dilator and a delivery sheath. It is preferred that the insertion device is an all-in-one device comprising a guide wire, a dilator and a delivery sheath. Within the context of the present invention, an all-in-one device comprises a device wherein the individual components are presented and/or attached together but are slidable and/or movable relative to one another. Advantageously, the use of an all-in-one device simplifies the procedure of inserting the insertion device, avoiding the requirement to insert multiple separate instruments which would require more manipulation and increase the risk of injury to the patient. Thus, the use of an all-in-one device advantageously avoids the need to repeatedly insert and retract separate instruments into and from the patient, thus reducing the risk of injuring the patient.

Preferably, the guide wire comprises an integrally formed puncture head. The guide wire advantageously enables the puncture of anatomical structures, for example, anatomical walls separating anatomical compartments, and is particularly advantageous for the puncture of outer walls of anatomical compartments with greater tissue resistance. The puncture head is typically shaped so as to present an extremely sharp end to allow the operator to have improved precision and control in a critical phase of the procedure. Such a sharp end would not normally be used because of the risk of accidental puncture and/or injury. However, in the present invention the insertion device is configured, as will be explained in further detail below, to prevent such accidents.

Preferably, the puncture head comprises a solid distal tip. In other words, in this embodiment the puncture head is not hollow or does not comprise a distal aperture like in a conventional vascular puncture-needle as this would create an unnecessarily larger incision and often will require the use of undesired force for successful puncture. Larger incisions are not desirable where dangerously high blood flows are expected. The use of a conventional needle is not recommended for an anatomical wall such as the aortic wall in view of the risk of aortic rupture. In other conventional methods, a standard guide wire might be used to perform the puncture step. However, standard guide wires have a rounded or flat head which does not permit accurate puncture and may be dangerous if they accidentally deflect from the anatomical wall to be punctured. Preferably, the puncture head comprises a conical distal tip. Preferably, the puncture head comprises a tapered distal tip. Advantageously, the provision of a tapered and/or conical tip allows the tip to push through and dilate the hole created in the atrium and aorta by the puncture wire.

Preferably, the puncture head is configured to facilitate the puncture of the anatomical wall, for example, the puncture head comprises a coring means or surface.

In one embodiment, the diameter at the base of the tip of the puncture head is substantially the same as the diameter of the guide wire. Such an arrangement provides for a smooth transition from the guide wire to the tip of the puncture head.

It is preferred that the insertion device comprises a dilator which is slidable relative to the guide wire. In one embodiment, the dilator may be retractable. Typically, the dilator is slidable along and/or around the guide wire. Advantageously, the dilator is configured such that it stretches the puncture made by the puncture head of the guide wire. Preferably, the dilator is incorporated with the guide wire. Preferably, the dilator extends along a portion of the length of the guide wire. Preferably, the length of the dilator of the invention is shorter than the length of known dilators. Advantageously, the dilator of the present invention is able to pass through an anatomical wall, avoiding the need to remove the dilator and/or use a separate dilator at a later stage. In one embodiment, the dimensions of the widest cross section of the puncture head are substantially the same as those of the distal end of the dilator. Such an arrangement advantageously provides for smooth transition from the puncture head to the dilator, thus allowing for smooth delivery of the insertion device.

Preferably, the insertion device comprises a delivery sheath which is slidable relative to the guide wire. Typically, the delivery sheath is slidable along and/or around the guide wire. Advantageously, the delivery sheath is configured to insert, deliver and/or position the intracorporeal device within a patient. Typically, during insertion of the intracorporeal device into a patient, the delivery sheath extends along the guide wire from the distal end of the outer sheath to the proximal end of the puncture head. In this extended configuration, the delivery sheath advantageously provides a passageway for insertion of the intracorporeal device. After puncture, delivery and implantation of the intracorporeal device, the delivery sheath may be retracted such that the distal end of the delivery sheath slides towards the distal end of the outer sheath, exposing the guide wire. Preferably, the guide wire, dilator and/or delivery sheath are movable relative to each other.

Within the context of the present invention, the term slidable means that one component slides along another. Thus, the dilator and/or the delivery sheath may slide along and/or around the guide wire during insertion and/or retraction of the insertion device into and/or from a patient.

Preferably, the system comprises one or more means for steering the outer sheath, delivery sheath, dilator and/or guide wire. Preferably, the insertion device comprises one or more means for steering the outer sheath, delivery sheath, dilator and/or guide wire. Preferably, the outer sheath, delivery sheath, dilator and/or guide wire comprise one or more means for steering the outer sheath, delivery sheath, dilator and/or guide wire. Advantageously, the means for steering the outer sheath, delivery sheath, dilator and/or guide wire facilitates control of the movement and/or position of these components of the system during insertion and/or retraction into or from a patient. Advantageously, the steering means improves the accuracy and precision of guiding and steering the system during insertion into a patient.

It is preferred that the steering means comprises one or more curved portions on the outer sheath, delivery sheath, dilator and/or guide wire. Typically, the provision of a curved portion on the delivery sheath and a curved portion on the outer sheath allows the delivery sheath and the outer sheath to be rotated independently of one another, thus providing for enhanced control of movement of the system during insertion and improving safety of insertion. Advantageously, the provision of a curved portion on the outer sheath enables movement of the combination of the delivery sheath and the guide wire during insertion. Advantageously, the provision of a curved portion on the delivery sheath assists in guiding the guide wire and dilator during insertion. Advantageously, the provision of a curved portion on the guide wire facilitates coiling of the guide wire. In a preferred embodiment, the guide wire is capable of coiling around the puncture head.

Preferably, the guide wire comprises a flexible distal portion adjacent the puncture head, and a more rigid proximal portion. These features are particularly advantageous in the prevention of injuries due to the sharpness of the puncture head. Once the puncture has been performed, the puncture head advances into a second anatomical compartment together with the dilator. The flexible portion of the guide wire becomes unsupported and coils around the anchored puncture head, so as to provide an effective shield between the puncture head and surrounding tissues. Preferably, the guide wire is made of a shape memory material so that the guide wire can be configured into a shield surrounding the puncture head.

Preferably, the insertion device further comprises a proximal handle for steering the outer sheath, delivery sheath, dilator and/or guide wire. Preferably, the steering handle comprises a rotation knob. Typically, the proximal handle is provided outside the body of the patient. Typically, the rotation knob may be rotated by an operator to control the movement and position of the transcatheter insertion system. In one embodiment, the rotation knob may be used to facilitate insertion and/or retraction of the system into and/or from the patient. Advantageously, the proximal steering handle provides for accurate control of the position and movement of the system during insertion into and retraction from a patient.

Preferably, the insertion device comprises a marker for detecting and/or visualising the position of the transcatheter insertion device. Typically, the marker comprises a material which may be detected during insertion of the insertion device. Typically, the marker is visible through X-ray, fluoroscopy, echocardiography and/or ultrasound techniques. Typically, the marker is provided on the guide wire, dilator, delivery sheath and/or the outer sheath. In one embodiment, the marker may be provided as a band. In one embodiment, the marker may comprise a metallic material which may be visualised by a user. Advantageously, the provision of a detection and/or visualisation means allows the operator to determine the position of the system during insertion, such that the user can adjust and control the position of the system to ensure that the system travels along the required path and does not accidentally perforate any veins or anatomical walls which may lead to injury.

It is preferred that the insertion device comprises means for detachably connecting to the intracorporeal device. Preferably, the insertion device comprises means for selectively attaching to and/or detaching from the intracorporeal device. Preferably, the delivery sheath comprises the means for detachably connecting to the intracorporeal device. Preferably, the connecting means comprises one or more retractable tabs. Preferably, the one or more retractable tabs are provided at a distal end of the delivery sheath.

Preferably, the intracorporeal device comprises a connector and/or a flow regulating device. The connector and/or flow regulating device of the present invention are as described in PCT Application No. PCT/EP2015/055578.

In one embodiment, the system may comprise a hemodialysis valve for the removal of excess blood from the patient. Typically, the hemodialysis valve further comprises a flush port to assist in the removal of excess blood.

According to a second aspect, there is provided a method for the transcatheter insertion of an intracorporeal device into a patient comprising the steps of: (a) puncturing at least one anatomical wall separating anatomical compartments; (b) delivering the intracorporeal device into the patient; and (c) implanting the intracorporeal device through the anatomical wall(s); wherein steps (a), (b) and (c) are carried out using a transcatheter insertion system according to the first aspect of the invention.

Preferably, the method comprises the step of guiding the insertion device using an outer sheath arranged and configured to provide a passageway for the intracorporeal device and/or the insertion device and means for guiding the insertion device. Preferably, the guiding means is positioned adjacent to or at a distal end of the outer sheath.

Preferably, the guiding means is substantially ring-shaped. It is preferred that the inner dimensions of the guiding means are smaller than the inner dimensions of the outer sheath. Preferably, the inner diameter of the guiding means is smaller than the inner diameter of the outer sheath.

Preferably, the guiding means comprises a substantially rigid material. Preferably, the guiding means comprises an inflatable balloon.

Preferably, the method comprises the step of detecting and/or visualising the system of the first aspect. Preferably, the step of detecting and/or visualising comprises the use of a marker provided on the guiding means, delivery sheath, outer sheath, dilator and/or guide wire. Preferably, the step of detecting and/or visualising is carried out using X-ray, fluoroscopy, echocardiography and/or ultrasound techniques.

Preferably, steps (a), (b) and (c) of the method are carried out using an all-in-one insertion device. Preferably, the all-in-one insertion device comprises a guide wire, a dilator and a delivery sheath. Preferably, the guide wire comprises an integrally formed puncture head. Preferably, the insertion device comprises a dilator which is slidable relative to the guide wire. It is preferred that the insertion device comprises a delivery sheath which is slidable relative to the guide wire. Preferably, the guide wire, dilator and delivery sheath are movable relative to each other.

Preferably, the method further comprises the step of pressing the outer and/or delivery sheath against the anatomical walls to facilitate puncture and provide support to the anatomical walls. The present invention is particularly advantageous in the case of the implantation of an intracorporeal device across two or more anatomical walls. For example, the outer sheath allows the anatomical walls to be pressed into contact before, during and after the implantation of the intracorporeal device, so as to close the space between the two anatomical walls. This allows the elimination of life threatening blood leaks into said space.

It is preferred that the method further comprises the step of dilating the puncture after step (a).

Preferably, the method comprises the step of steering the outer sheath, delivery sheath, dilator and/or guide wire using steering means. Preferably, the steering means comprises one or more curved portions on the outer sheath, delivery sheath, dilator and/or guide wire.

Typically, the steering means comprises a proximal handle. Preferably, the steering handle comprises a rotation knob. Typically, the rotation knob which may be rotated by an operator to steer the outer sheath, delivery sheath and/or guide wire, thus controlling the position of the system during insertion and/or retraction.

Preferably, the method comprises the step of securing the intracorporeal device to the distal end of the insertion device prior to and/or during step (b). Preferably, the method comprises the step of detaching the intracorporeal device from the insertion device following step (c). Preferably, the step of securing is carried out using one or more retractable tabs, preferably provided at the distal end of the delivery sheath.

Preferably, the intracorporeal device comprises a connector and/or a flow regulator device.

The present invention is particularly advantageous when one or both compartments are compartments of the circulatory system. The preferred embodiment concerns a left atrium-aorta procedure. However, other compartment pairs are envisaged including, but not limited to, right ventricle-aorta, left ventricle-aorta, right atrium-vena cava superior, left atrium-aorta descending, left atrium-aorta ascending, right ventricle-pulmonary artery. Alternatively or additionally, one or both compartments may be compartments within the thoracic cavity or the abdomen.

The present invention is particularly useful for use in the treatment of heart failure, diastolic heart failure, systolic heart failure, left ventricle failure, right ventricle failure, paediatric heart anomalies and/or shunts.

Preferably, the at least one anatomical wall is an outer wall of the compartment. Preferably, the anatomical walls are the roof of the left atrium and the aortic wall.

According to a third aspect of the invention, there is provided an insertion device as specified in the first aspect.

According to a fourth aspect, there is provided an outer sheath comprising a guiding means as specified in the first aspect.

In this application, the terms "proximal" and "distal" are used relative to the medical professional, e.g. the proximal end is the end nearest the medical professional and the distal end is the part of the device that is inserted first into the patient.

Within the context of the invention, transcatheter includes percutaneous, trans-atrial, trans-femoral (through the leg), trans-apical (in the chest between the ribs), and trans-aortic (in the upper chest). Preferred embodiments are percutaneous systems, devices and methods.

LIST OF EMBODIMENTS

The following is a non-limiting list of potential embodiments of the present invention, set forth as embodiment groups (each an "Embodiment"). Additional embodiments of the invention are possible, as set forth throughout this specification and the drawings.

Embodiment 1

A transcatheter insertion system for the insertion of an intracorporeal device using an insertion device, wherein the system comprises an outer sheath arranged and configured to form a passageway for the intracorporeal device and/or the insertion device and said outer sheath comprises means for guiding the insertion device.

Embodiment 2

The system according to Embodiment 1, wherein the guiding means is positioned adjacent to or at a distal end of the outer sheath.

Embodiment 3

The system according to Embodiment 1 or 2, wherein the guiding means is substantially ring-shaped.

Embodiment 4

The system according to any preceding Embodiment, wherein the inner dimensions of the guiding means is smaller than the inner dimensions of the outer sheath.

Embodiment 5

The system according to any preceding Embodiment, wherein the guiding means comprises a substantially rigid material.

Embodiment 6

The system according to any one of Embodiments 1 to 4, wherein the guiding means comprises an inflatable balloon.

Embodiment 7

The system according to any preceding Embodiment, wherein the guiding means comprises a detection and/or visualisation means.

Embodiment 8

The system according to Embodiment 7, wherein the guiding means comprises a material visible by means of any one of X-ray, fluoroscopy, echocardiography and/or ultrasound techniques.

Embodiment 9

The system according to any preceding Embodiment, wherein the insertion device comprises one or more of a guide wire, a dilator and a delivery sheath.

Embodiment 10

The system according to any preceding Embodiment, wherein the insertion device is an all-in-one device comprising a guide wire, a dilator and a delivery sheath.

Embodiment 11

The system according to Embodiment 9 or 10, wherein the guide wire comprises an integrally formed puncture head.

Embodiment 12

The system according to any one of Embodiments 9 to 11, wherein the insertion device comprises a dilator which is slidable relative to the guide wire.

Embodiment 13

The system according to any one of Embodiments 9 to 12, wherein the insertion device comprises a delivery sheath which is slidable relative to the guide wire.

Embodiment 14

The system according to any one of Embodiments 9 to 13, wherein the guide wire, dilator and delivery sheath are movable relative to each other.

Embodiment 15

The system according to any one of Embodiments 9 to 14, further comprising one or more means for steering the outer sheath, delivery sheath, dilator and/or guide wire.

Embodiment 16

The system according to Embodiment 15, wherein the steering means comprises one or more curved portions on the outer sheath, delivery sheath, dilator and/or guide wire.

Embodiment 17

The system according to Embodiment 15 or 16, further comprising a proximal handle for steering the outer sheath, delivery sheath, dilator and/or guide wire.

Embodiment 18

The system according to Embodiment 17, wherein the steering handle comprises a rotation knob.

Embodiment 19

The system according to any preceding Embodiment, wherein the insertion device comprises a marker for detecting and/or visualising the position of the transcatheter insertion device.

Embodiment 20

The system according to Embodiment 19, wherein the marker is visible through X-ray, fluoroscopy, echocardiography and/or ultrasound techniques.

Embodiment 21

The system according to Embodiment 19 or 20, wherein the marker is provided on or in the guide wire, dilator, delivery sheath and/or or the outer sheath.

Embodiment 22

The system according to any preceding Embodiment, wherein the insertion device comprises means for detachably connecting to the intracorporeal device.

Embodiment 23

The system according to Embodiment 22, wherein the insertion device comprises means for selectively attaching and/or detaching from the intracorporeal device.

Embodiment 24

The system according to Embodiment 22 or 23, wherein the connecting means comprises one or more retractable tabs.

Embodiment 25

The system according to any preceding Embodiment wherein the intracorporeal device comprises a connector and/or a flow regulating device.

Embodiment 26

A method for the transcatheter insertion of an intracorporeal device into a patient comprising the steps of:
(a) puncturing at least one anatomical wall separating anatomical compartments;
(b) delivering the intracorporeal device into the patient; and
(c) implanting the intracorporeal device through the anatomical wall(s);
wherein steps (a), (b) and (c) are carried out using a transcatheter insertion system according to any one of Embodiments 1 to 25.

Embodiment 27

The method according to Embodiment 26, comprising the step of guiding the insertion device using an outer sheath arranged and configured to provide a passageway for the intracorporeal device and/or the insertion device and means for guiding the insertion device.

Embodiment 28

The method of Embodiment 27, wherein the guiding means is positioned adjacent to or at a distal end of the outer sheath.

Embodiment 29

The method of Embodiment 27 or 28, wherein the guiding means is substantially ring-shaped.

Embodiment 30

The method according to any one of Embodiments 27 to 29, wherein the inner dimensions of the guiding means is smaller than the inner dimensions of the outer sheath.

Embodiment 31

The method according to any one of Embodiments 27 to 30, wherein the guiding means comprises a substantially rigid material.

Embodiment 32

The method according to any one of Embodiments 27 to 30, wherein the guiding means comprises an inflatable balloon.

Embodiment 33

The method according to any one of Embodiments 26 to 32, further comprising the step of detecting and/or visualising the system of any one of Embodiments 1 to 25.

Embodiment 34

The method according to Embodiment 33, wherein the step of detecting and/or visualising comprises the use of a marker provided on the guiding means, delivery sheath, outer sheath, dilator and/or guide wire.

Embodiment 35

The method according to Embodiment 32 or 33, wherein the step of detecting and/or visualising is carried out using X-ray, fluoroscopy, echocardiography and/or ultrasound techniques.

Embodiment 36

The method according to any one of Embodiments 26 to 35, wherein steps (a), (b) and (c) are carried out using an all-in-one insertion device.

Embodiment 37

The method according to Embodiment 36, wherein the all-in-one insertion device comprises a guide wire, a dilator and a delivery sheath.

Embodiment 38

The method according to any one of Embodiments 26 to 37, wherein the guide wire comprises an integrally formed puncture head.

Embodiment 39

The method according to any one of Embodiments 26 to 38, wherein the insertion device comprises a dilator which is slidable relative to the guide wire.

Embodiment 40

The method according to any one of Embodiments 26 to 39, wherein the insertion device comprises a delivery sheath which is slidable relative to the guide wire.

Embodiment 41

The method according any one of Embodiments 26 to 40, wherein the guide wire, dilator and delivery sheath are movable relative to each other.

Embodiment 42

The method according to any one of Embodiments 26 to 41, further comprising the step of pressing the outer and/or delivery sheath against the anatomical walls to facilitate puncture and provide support to the anatomical walls.

Embodiment 43

The method according to any one of Embodiments 26 to 42, further comprising the step of dilating the puncture after step (a).

Embodiment 44

The method according to any one of Embodiments 26 to 43, comprising the step of steering the outer sheath, delivery sheath, dilator and/or guide wire using steering means.

Embodiment 45

The method according to Embodiment 44, wherein the steering means comprises one or more curved portions on the outer sheath, delivery sheath, dilator and/or guide wire.

Embodiment 46

The method according to Embodiment 44 or 45, wherein the steering means comprises a proximal handle.

Embodiment 47

The method according to Embodiment 46, wherein the steering handle comprises a rotation knob.

Embodiment 48

The method according to any one of Embodiments 26 to 47, comprising the step of securing the intracorporeal device to the distal end of the insertion device prior to and/or during step (b).

Embodiment 49

The method according to any one of Embodiments 26 to 48, comprising the step of detaching the intracorporeal device from the insertion device following step (c).

Embodiment 50

The method according to Embodiment 48 or 49, comprising the use of one or more retractable tabs.

Embodiment 51

The method according to any one of Embodiments 26 to 50, wherein the intracorporeal device comprises a connector and/or a flow regulator device.

Embodiment 52

An insertion device as specified in any one of Embodiments 1 to 25.

Embodiment 53

An outer sheath comprising a guiding means as specified in any one of Embodiments 1 to 25.

In the above list of embodiments of the invention, each listed Embodiment, as a group of embodiments, comprises a single specific embodiment and/or plural specific embodiments, as specified in the particular combination of embodiments for each Embodiment group.

BRIEF DESCRIPTION OF THE DRAWINGS

The invention will be further described with reference to the drawings and figures, in which.

DETAILED DESCRIPTION

The invention is described by way of examples, which are provided for illustrative purposes only. These examples should not be construed as intending to limit the scope of protection that is defined in the claims. For example, although various aspects have been described with respect to the heart and the circulatory system, this is not intended to be limiting, and is merely performed to provide an example of implementation. Aspects disclosed herein may be utilised in any medical device implantable within the human body, for example in the cardiovascular system, respiratory system, gastric system, neurological system, and the like, some examples including implantable pumps and drug delivery pumps. As used herein, the term "means" can be equivalently expressed as, or substituted with, any of the following terms: device, apparatus, structure, part, sub-part, assembly, sub-assembly, machine, mechanism, article, medium, material, appliance, equipment, system, body or similar wording.

Figure 1:
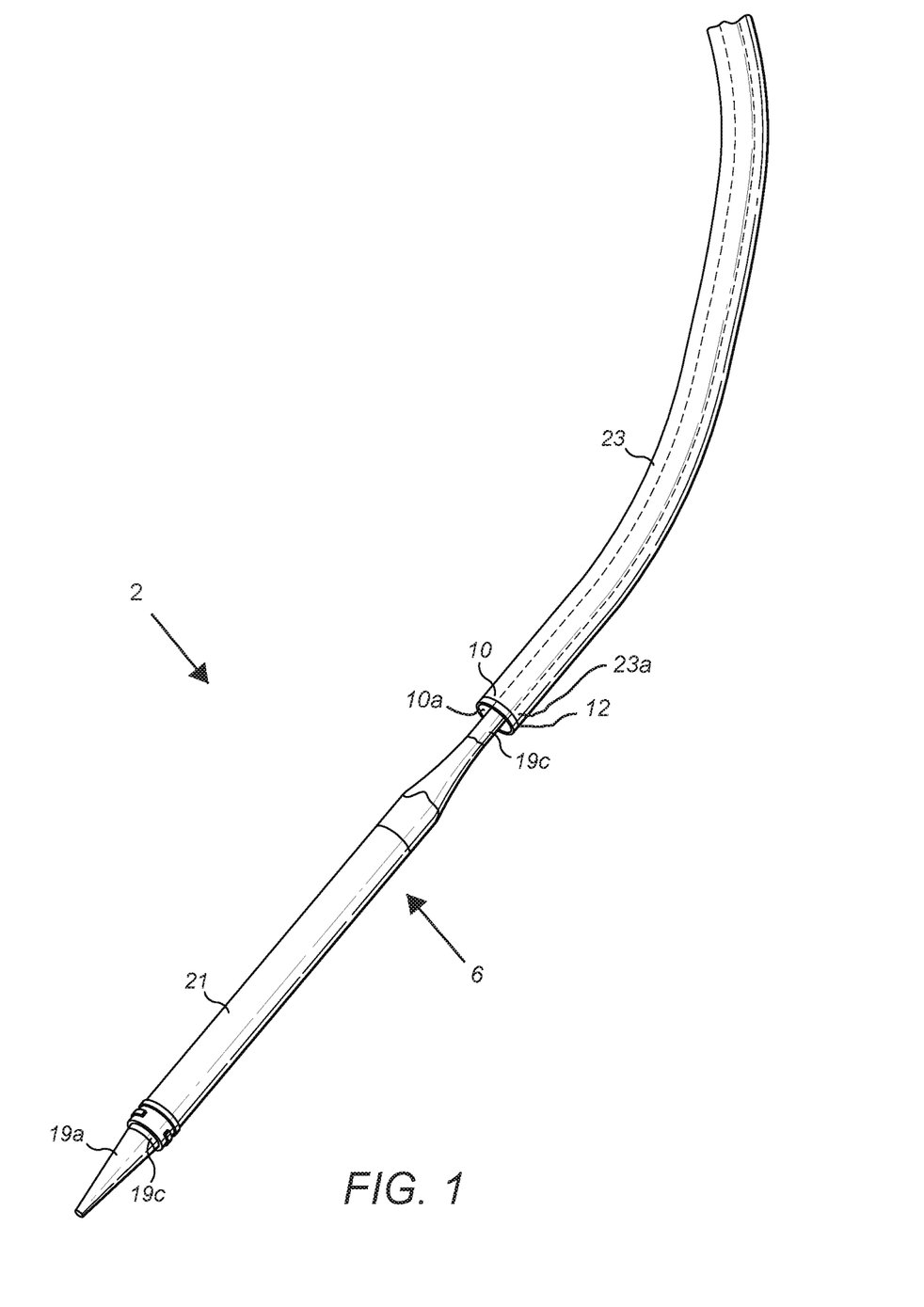
FIG. 1 is a schematic representation of a system according to the present invention.

Referring to FIG. 1, there is illustrated a transcatheter insertion system 2 for the insertion of an intracorporeal device 4 using an insertion device 6, wherein the system comprises an outer sheath 23 having a distal opening 23*a* and arranged and configured to form a passageway for the intracorporeal device 4 and/or the insertion device 6 and said outer sheath 23 comprises means for guiding 10 the insertion device. The guiding means 10 defines an opening 10*a* and is positioned adjacent to or at a distal end of the outer sheath 23, allowing for more accurate and precise control of the movement and position of the insertion device 6 during insertion into a patient.

In the embodiment shown in FIG. 1, the guiding means 10 is substantially ring-shaped and has a doughnut shape. It has been found that the provision of a guiding means 10 having a ring shape enables enhanced control over movement of the insertion device 6 when inserted into a patient. The guiding means 10 has an outer diameter such that it fits inside the diameter of the outer sheath 23. In the embodiment wherein the guiding means 10 has a doughnut shape, the inner diameter of the guiding means 10 is smaller than the inner diameter of the outer sheath 23, narrowing the exit from the outer sheath 23 such that the insertion device 6 is guided out of the outer sheath 23 substantially along or close to the central axis of the outer sheath 23. This allows for greater control of the movement and position of the insertion device 6 when inserted into a patient. Advantageously, in the embodiment wherein the guiding means has a doughnut shape, the system is more forgiving of the operator's uncontrolled manipulations, wherein such movements translate into smaller movements of the insertion device which allow for improved accuracy and precision during insertion.

In the embodiment shown in FIG. 1, the guiding means 10 comprises a substantially rigid material and is made of a biocompatible polymer. In another embodiment, the guiding means may comprise an inflatable balloon.

The guiding means 10 comprises a detection and/or visualisation means in the form of a marker 12. The marker 12 is provided as a band on the guiding means and comprises a material visible by means of any one of X-ray, fluoroscopy, echocardiography and/or ultrasound techniques. The marker 12 allows the operator to detect the position of the system 2 during insertion such that the operator can adjust the position of the system 2 to make sure that it follows the correct path and does not accidentally puncture any veins or anatomical walls that may lead to injury.

In the embodiment shown in FIG. 1, the insertion device 6 is an all-in-one device comprising a guide wire 19b, a dilator 19c and a delivery sheath 21. Advantageously, in this embodiment, the guide wire 19b, dilator 19c and delivery sheath 21 are presented and/or attached together but are slidable relative to one another. Thus, the all-in-one device 6 simplifies the procedure of inserting the insertion device, avoiding the need to repeatedly insert and retract separate instruments into and from the patient, thus reducing the risk of injuring the patient, for example, by accidentally puncturing the inferior vena cava.

As will be described in more detail below, the puncture head 19a is used to puncture one or more anatomical walls; the guide wire 19b to direct the elements during insertion; the dilator 19c to stretch punctures made by the puncture head 19a; the delivery sheath 21 to insert, deliver and position an intracorporeal device 4 and the outer sheath 23 to form a safe passageway for inserting the insertion device and intracorporeal device 4. The guiding means 10 advantageously provides for enhanced accuracy and precise control of the position of the insertion device 6 and/or intracorporeal device 4 during delivery and/or implantation into a patient.

Thus, the insertion device 6 enables the creation of a safe pathway for the delivery and implantation of an intracorporeal device 4. More specifically, the insertion device 6 is particularly advantageous for the puncture of an anatomical wall, such as an outer wall of an anatomical compartment which has a greater tissue resistance. The insertion device also enables a particularly accurate and small incision to be created, which is crucial in incisions involving high pressure blood flow. A preferred use of the insertion device 6 is for the puncture of outer walls of internal organs, for example for an extra-cardiac puncture.

The guide wire 19b comprises an integrally formed puncture head 19a. The puncture head 19a comprises a solid, tapered distal tip. In this embodiment, the puncture head 19a is connected to the distal end of the guide wire 19b for example by welding. The puncture head 19a has a solid tip, i.e. devoid of a hollow channel as observed in standard insertion or injection needles. The puncture head 19a is conically shaped and forms an extremely sharp tip. In one embodiment, the diameter at the base of the conical puncture head 19a is larger than that of the guide wire 19b. The guide wire 19b is slidable through a dilator 19c. The diameter at the base of the conical puncture head 19a is substantially equal to that of the distal end of the dilator 19c so as to create a flush, smooth transition.

In an alternative embodiment (not shown), the diameter at the base of the conical puncture head 19a is substantially the same as that of the guide wire 19b so that the guide wire 19b is a tapered guide wire with a sharp conical tip. In this alternative embodiment, the puncture head 19a and the guide wire 19b are integrally formed. A diameter of the guide wire 19b is substantially equal to that of the distal end of the dilator so as to create a flush, smooth transition; although in this case, the dilator 19c may not be required as the tapered guide wire 19b can act as a needle.

The use of a sharp puncture head 19a at the distal end of the guide wire 19b allows the insertion device 6 to act as an atraumatic and accurate puncture device. The relative dimensions of the puncture head 19a, the guide wire 19b and the dilator 19c enable the size of the puncture to be gradually and gently increased.

The guide wire 19b comprises a dilator 19c which is slidable relative to the guide wire. The dilator may be retractable and may be slidable along and/or around the guide wire. The dilator 19c is configured such that it stretches the puncture made by the puncture head of the guide wire. The dimensions of the widest section of the puncture head 19a are substantially the same as those of the distal end of the dilator 19c. This arrangement advantageously provides for smooth transition from the puncture head 19a to the dilator 19c, thus allowing for smooth delivery of the insertion device 6. In the embodiment shown in FIG. 2B, the dilator 19c is short in length when compared with the length of known dilators, facilitating passage of the dilator through an anatomical wall of the patient.

Figure 2A:
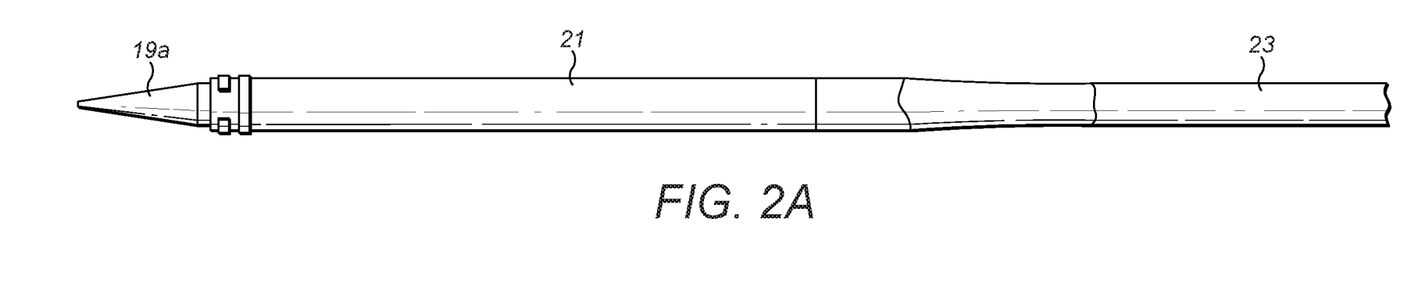
FIG. 2*a* is a schematic representation of a system according to an embodiment of the invention.
Figure 2B:
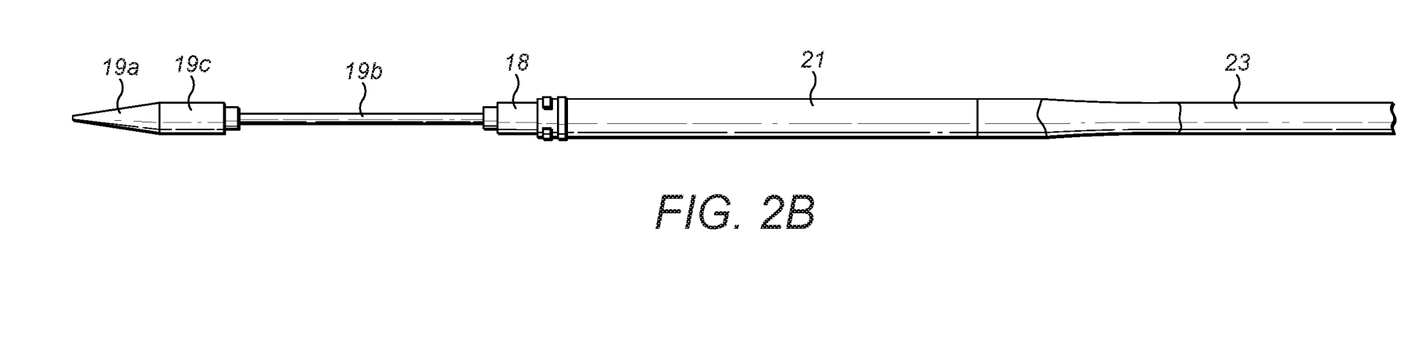
FIG. 2*b* is a schematic representation of a system according to another embodiment of the invention.

The delivery sheath 21 of the insertion device 6 is slidable relative to the guide wire 19b. The delivery sheath 21 may advantageously be slidable along and/or around the guide wire. The guide wire 19b, dilator 19c and/or delivery sheath 21 are movable relative to each other. FIG. 2A shows an embodiment wherein the delivery sheath 21 is in the insertion position, i.e. wherein the delivery sheath 21 covers the guide wire 19b and extends from the distal end of the outer sheath 23 to the proximal end of the puncture head 19b. In this embodiment, the delivery sheath 21 provides a passageway for insertion of the intracorporeal device 4 FIG. 2B shows an embodiment wherein the delivery sheath 21 is in a retracted position, i.e. the delivery sheath 21 extends from the distal end of the outer sheath 23 and partially covers the guide wire 19b. The delivery sheath 21 may adopt the retracted position following delivery and implantation of the intracorporeal device 4.

With reference to FIG. 1, the outer sheath 23, delivery sheath 21 and/or guide wire 19b comprise one or more means for steering the transcatheter insertion system, wherein the steering means comprises one or more curved portions 14 on the outer sheath 23, delivery sheath 21, dilator 19c and/or guide wire 19b. The provision of a curved portion on the outer sheath 23 enables movement of the combination of the delivery sheath 21 and the guide wire 19b during insertion. The provision of a curved delivery sheath 21 assists in guiding the guide wire 19b and dilator 19c during insertion. The provision of a curved portion 14 on the guide wire 19b facilitates coiling of the guide wire 19b.

Figure 5:
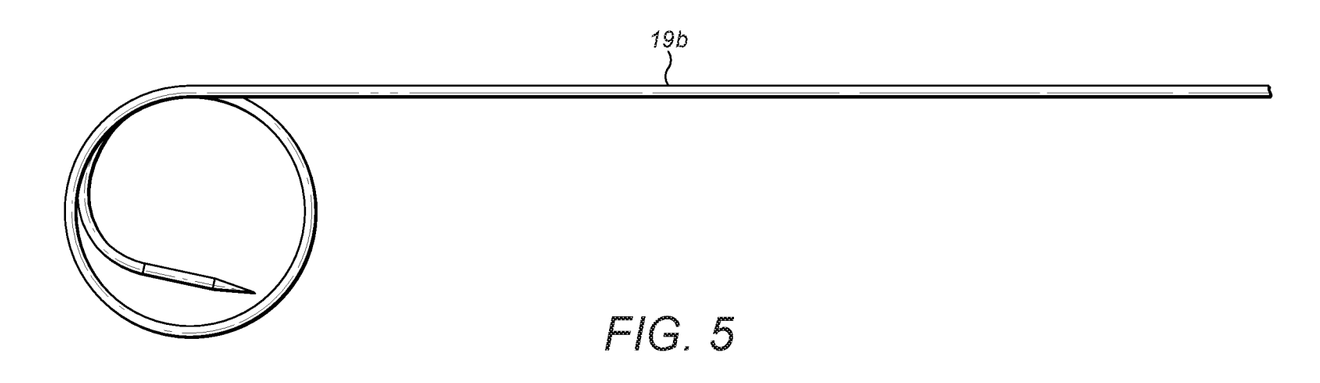
FIG. 5 is a schematic representation of a guide wire according to the invention.

As can be seen in FIG. 5, the guide wire 19b is capable of coiling around the puncture head 19a. The guide wire 19b comprises a flexible distal portion adjacent the puncture head 19a, and a more rigid proximal portion. These differences in rigidity enable the manipulation and guiding of the guide wire through the patient's anatomy and are particularly advantageous in the prevention of injuries due to the sharpness of the puncture head 19a. Once the puncture has been performed, the puncture head 19a advances into a second anatomical compartment together with the dilator 19c. As shown in FIG. 5, the flexible portion of the guide wire 19b coils around the anchored puncture head 19a, so as to provide an effective shield between the puncture head 19a and surrounding tissues. The guide wire 19b is typically made of a shape memory material so that the guide wire can be configured into a shield surrounding the puncture head 19a. In this embodiment, the length of the puncture head 19a is selected such that it is long enough to penetrate the atrial and aortic walls before looping, and short enough such that it does not puncture the opposite side of the aortic wall after the initial puncture. The diameter of the loop created by the guide wire 19b in the coiled configuration is typically smaller than the inner diameter of the aorta and large enough to protect the sharp tip of the puncture head 19a from damaging the aortic tissues.

Figure 3:
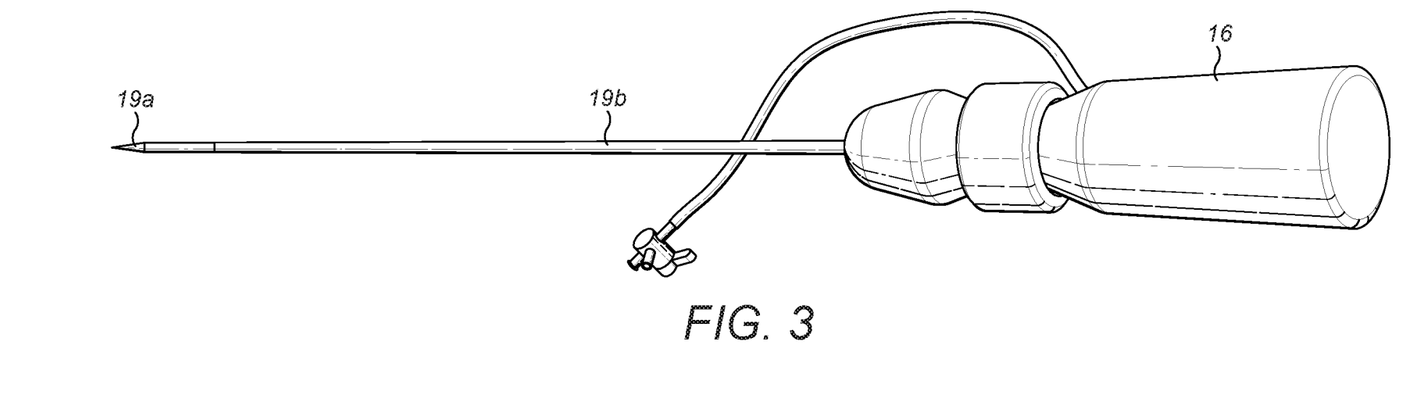
FIG. 3 is a schematic representation of a system according to a further embodiment of the invention.
Figure 4:
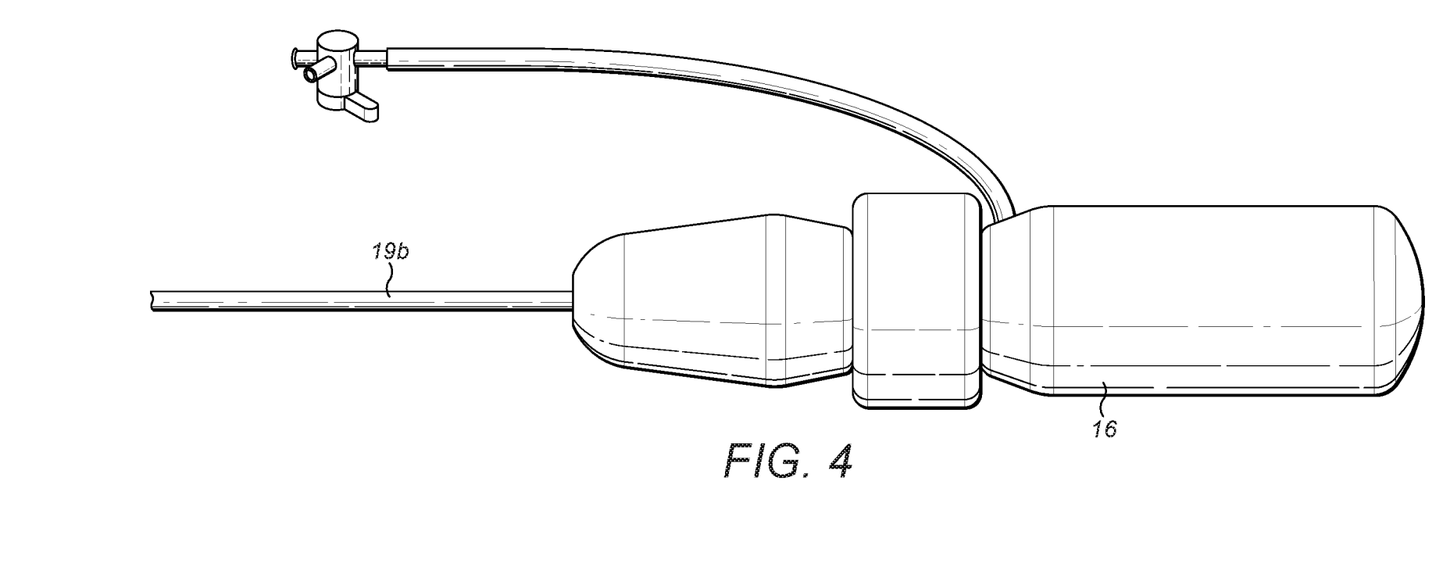
FIG. 4 is a schematic representation of the proximal handle of the system of the invention.

The insertion device further comprises a proximal handle 16 for steering the outer sheath 23, delivery sheath 21, dilator 19c and/or the guide wire 19b. Preferably, the proximal handle is provided in the form of a rotation knob 16 which may be manipulated by an operator such as a medical professional to control the movement of the system 2 within a patient. In one embodiment, the rotation knob 16 may be used to facilitate insertion and/or retraction of the insertion device 6 into and/or from a patient. The rotation knob 16 is positioned outside the body of the patient and may be attached to the other components of the system via the guide wire 19b. FIG. 3 shows the position of the rotation knob 16 with respect to the guide wire 19b and puncture head 19a. FIG. 4 shows the rotation knob 16 which may be rotated by an operator to control the movement of the system 2. The provision of a rotation knob 16 advantageously provides for accurate and precise control of the movement of the system 2 when inserted within a patient.

In another embodiment, the system 2 may comprise a marker for detecting and/or visualising during insertion and/or implantation, wherein the marker comprises a material which is visible through X-ray, fluoroscopy, echocardiography and/or ultrasound techniques. The marker may be provided on the guide wire 19b, dilator 19c, delivery sheath 21 and/or the outer sheath 23. The marker may be provided in the form of a metallic band on the outer sheath 23, delivery sheath 21, dilator 19c and/or guide wire 19b. The marker 12 advantageously allows the operator to detect the position of the system 2 when inserted in a patient such that the operator can move the system 2 accordingly, reducing the risk of injuring the patient.

With reference to FIG. 2B, the insertion device comprises means for detachably connecting to the intracorporeal device 4, wherein the connecting means comprises one or more retractable tabs 18. Preferably, the one or more retractable tabs 18 are provided at the distal end of the delivery sheath 21. Advantageously, the one or more tabs 18 hold the connector 7 in position during delivery and implantation of the intracorporeal device 4. Preferably, the tabs 18 are provided to hold an anchor component of the connector 7 in place during deployment of the intracorporeal device 4.

Figure 6:
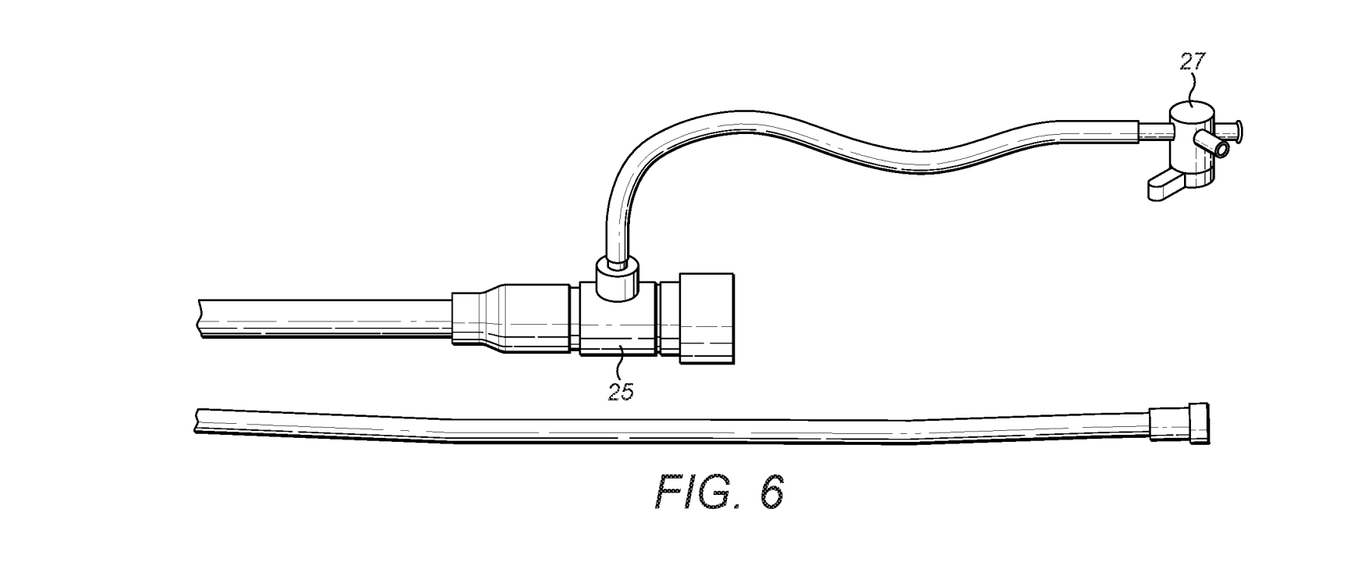
FIG. 6 is a schematic representation of a hemostasis valve which may be used with a system according to the invention.

With reference to FIG. 6, the system may further comprise a hemodialysis valve 25 comprising a flush port 27 for the removal of excess blood from the patient.

Figure 7:
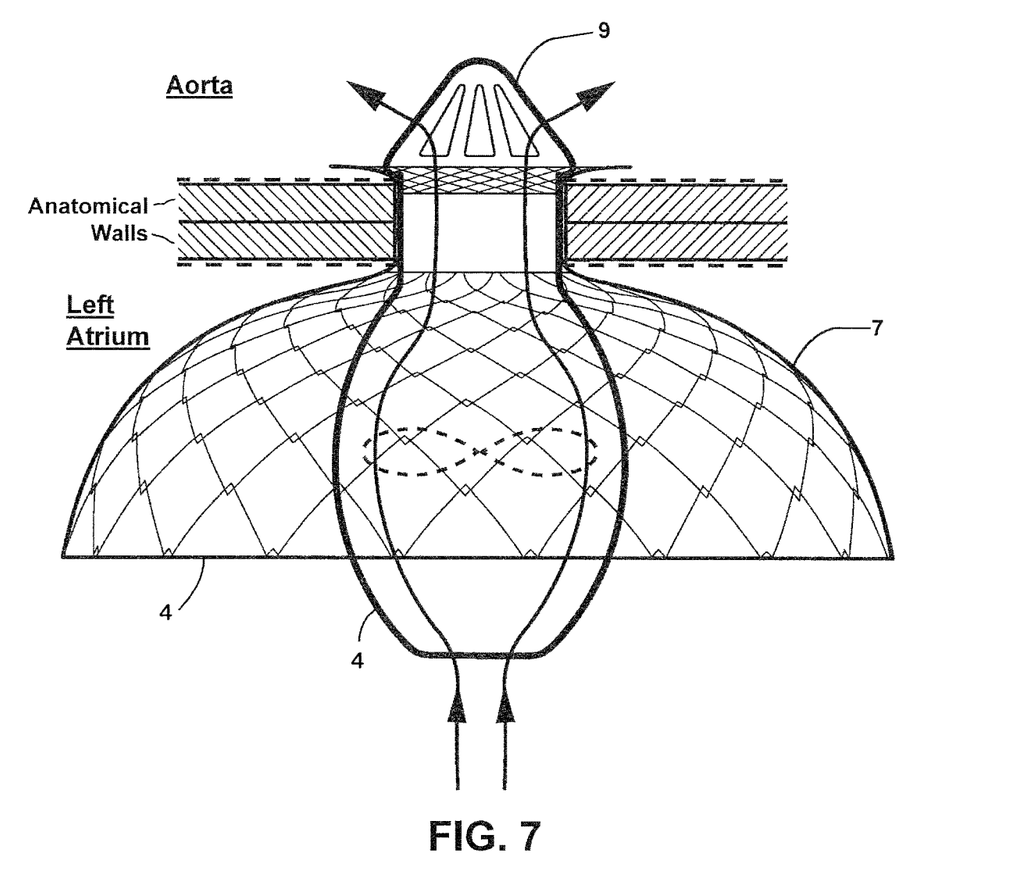
FIG. 7 is a schematic representation of a connector and flow regulating device according to the invention disposed across anatomical walls.

The intracorporeal device 4 comprises an intracorporeal connector 7 and an intracorporeal flow regulating device 9. Advantageously, the connector 7 is able to preserve the integrity of the anatomical structure and tissues against the pressure exerted by the fluid (blood) flow and the flow regulating device 9, thereby preventing the collapse of the compartment(s). The connector and the flow regulating device of the present invention are as described in PCT Application No. PCT/EP2015/055578.

The system 2 of the present invention advantageously allows the puncture of anatomical walls and the insertion of a sheath or catheter through the patient's anatomy for subsequent introduction of an intracorporeal device 4. The present invention is particularly advantageous in procedures involving insertion and implantation through two anatomical walls. This is because the insertion device 6 can push one wall in contact with the other so that puncture and subsequent insertion and implantation are facilitated.

A method according to the present invention will now be described by way of example. With reference to the figures, there is provided a method for the transcatheter insertion of an intracorporeal device 4 into a patient comprising the steps of: (a) puncturing at least one anatomical wall separating anatomical compartments; (b) delivering the intracorporeal device 4 into the patient; and (c) implanting the intracorporeal device 4 through the anatomical wall(s); wherein steps (a), (b) and (c) are carried out using a transcatheter insertion system 2 according to the first aspect of the invention.

The method comprises the use of an all-in-one insertion device 6 comprising a guide wire 19b, a dilator 19c and a delivery sheath 21. The all-in-one insertion device 6 is used to carry out the steps of intracorporeal puncture, delivery and implantation of an intracorporeal device 4 into a patient. Thus, the method advantageously allows the use of a single device for both the puncturing step and the insertion/delivery and implantation steps of the procedure. In the present invention, the puncture is made with the distal end of the guide wire, and in particular with the puncture head 19a of the guide wire 19b. This allows for a gradual, atraumatic and accurate incision to be made and this is particularly advantageous when puncturing outer walls of anatomical compartments, for example for cardiac to extra-cardiac puncture such as from one heart compartment heart into a major blood vessel.

The first step is the insertion of a guide wire 19b, wherein a needle carrying a guide wire is placed on the groin area of the patient, adjacent the femoral artery. Pressure is applied so that the patient's skin is punctured by the tip of the needle and pushed through the skin and tissues into the femoral artery. Once in place, the guide wire is advanced along the femoral artery and up the inferior vena cava. The guide wire 19b exits the inferior vena cava and enters the right atrium. Next, a large and steerable outer sheath 23 can be deployed into the left atrium over the wire to facilitate the following steps of the procedure. A delivery sheath 21 is deployed within the outer sheath, wherein the guide wire 19b passed through the delivery sheath 21.

The guide wire 19b comprises a relatively flexible (distal) portion adjacent to the puncture head before a more rigid proximal portion, so that as the guide wire 19b folds upon itself at the flexible portion, thereby forming a U-shape. The flexible portion now advances first, followed by the rigid proximal portion. Thus, the guide wire 19b can be moved atraumatically through the delivery sheath or alternatively, through the patient's blood vessels. The guide wire 19b can be straightened when required by gently pulling the proximal end and repositioning the distal portion at its front most position. The puncture head 19a is pulled back towards the distal end of the dilator 19c.

The next step is the extra-cardiac puncture of the left atrium using an insertion device according to the present invention. The distal end of the outer sheath 23 is placed against the roof of the left atrium 3 and pushed against the wall so that the roof of the left atrium 3 contacts the aortic wall. The puncture head 19a is advanced so as to puncture the roof of the left atrium 3. This sharp, conical shape enables the medical professional to create a small and accurate extra-cardiac incision in a smooth and atraumatic manner. The puncture head 19a and dilator 19c are advanced through the puncture towards the aortic wall. The outer sheath 23 is used to push the wall of the left atrium against the aortic wall and hold both walls together to assist puncture of the aortic wall. Once the aortic wall is pierced, the dilator 19c can stretch both punctures to facilitate the insertion of the delivery sheath 21. The dilator 19c, guide wire 19b and delivery sheath 21 may be left in place in the aorta. The outer sheath 23 can remain in the left atrium.

The puncture head 19a is advanced further into the aorta. The flexible portion of the guide wire 19b typically coils around the puncture head 19a, thereby anchoring and shielding the puncture head 19a from surrounding tissues.

It can therefore be seen that the outer sheath 23 can be used to safely deliver the intracorporeal devices but also assists the puncture of the anatomical wall(s), in particular when the procedure involves the puncture of more than one anatomical wall.

The next step is the delivery of an intracorporeal device 4 such as a connector 7. The intracorporeal connector 7 is delivered in a folded or compressed state into the delivery sheath 21 along the guide wire 19b. When the connector 7 reaches the roof of the left atrium, it is pushed along the guide wire 19b, through the incision in the anatomical walls until the neck of the connector is correctly positioned across the anatomical walls and the anchor and shield of the connector are deployed on either side of the walls in the aorta and the left atrium, respectively. The connector 7 gradually expands at it exits the distal end of the delivery sheath 21.

The next step is the insertion of an intracorporeal flow regulating device 9 which may be inserted and advanced through the sheath 21 and along the guide wire 19b until it reaches the connector 7. The distal portion and more particularly the distal tip of the connector 7 acts as an actuator which opens a gate in the neck of the connector 7 by stretching the opening of the gate. An intermediate portion of the flow regulating device 9 sits in the neck of the connector 7 and is securely positioned. The flow regulating device 9 can be secured due to the pressure of the resilient material of the gate and by ribs. Additionally or alternatively, the flow regulating device 9 can be secured by screwing the intermediate portion of the flow regulating device 9 to the neck of the connector 7. This screwing mechanism also enables the safe and guided advancement of the flow regulating device 9 into the connector 7. Where provided, sealing means prevent any leakage through the coupling interface between the flow regulating device 9 and the connector 7.

The provision of a guiding means 10 at the distal end of the outer sheath 23 provides for improved accuracy and precision of control of the movement of the insertion device 6 during insertion into a patient. Furthermore, the guiding means 10 has a doughnut shape such that the inner diameter of the guiding means 10 is smaller than the inner diameter of the outer sheath 23. The doughnut shape of the guiding means 10 therefore narrows the exit at the distal end of the outer sheath 23, such that the insertion device 6 is guided out of the outer sheath 23 substantially along or close to the central axis of the outer sheath 23. Thus, the provision of a guiding means 10 having a doughnut shape is more forgiving of uncontrolled movements that may be made by the operator, thus improving safety of the system 2, for example, reducing the possibility of accidentally puncturing an anatomical wall. Furthermore, the provision of a curved outer sheath 23 and/or a curved delivery sheath 21 and/or guide wire 21, and the provision of a proximal handle 16 comprising a rotation knob also assist in controlling the movement of the insertion device 6 during insertion into a patient.

The method further comprises the step of detecting and/or visualising the system 2 during delivery and implantation into a patient. The step of detecting and/or visualising comprises the use of a marker 12 provided on the guiding means 10, wherein the marker 12 comprises a metallic material which may be detected using techniques such as X-ray, fluoroscopy, echocardiography, ultrasound techniques. In another embodiment, the marker 12 may be provided on the outer sheath 23, delivery sheath 21 and/or the guide wire 19b. The marker 12 allows for detection of the position of the system 2, thus allowing the operator to adjust the position of the system 2 accordingly.

The method further comprises the step of detaching the intracorporeal device 4 from the insertion device 6 following implantation of the intracorporeal device 4 into a patient. In one embodiment, the connector 7 may be detached from the tabs 18 at the distal end of the delivery sheath 21, causing expansion of the connector into an activated position.

The system 2 may now be retracted from the patient. The rotation knob 16 may be used to assist in retraction of the system 2 from the patient, leaving the intracorporeal device in position.

Although the present invention has been described with respect to a left atrium to aorta procedure, the system and method can also be applied to other delivery sites including, but not limited to, right atrium-aorta, vena cava-pulmonary artery, vena cava-aorta. Thus, the present invention can be broadly applied for example as left ventricular assist devices (LVAD), right ventricular assist devices (RVAD) or biventricular assist devices (BiVAD), for cardiopulmonary support (CPS) or for intra-corporeal membrane oxygenation (ICMO) or bubble oxygenation, for the treatment of other organs with pressure issues (e.g. gastric or neurological procedures). The present invention is versatile and a wide variety of applications can therefore be envisaged.

The invention claimed is:

1. A transcatheter insertion system for the insertion of an intracorporeal device using an insertion device, comprising:
    an insertion device,
    an outer sheath arranged and configured to form a passageway for the intracorporeal device and/or the insertion device, and
    a guiding means for guiding the insertion device, wherein the guiding means is a substantially ring-shaped element having a doughnut shape, and wherein an outer diameter of the doughnut shape of the guiding means fits inside a diameter of the passageway formed by the outer sheath and said guiding means defines an opening which is narrower than a distal opening of the passageway formed by the outer sheath, wherein the guiding means is positioned adjacent to or at a distal end of the outer sheath,
    wherein the insertion device further comprises a guide wire and wherein the guide wire comprises an integrally formed puncture head, wherein the puncture head is formed at a distal end of the guide wire and comprises a tapered distal tip, such that the puncture head is configured to facilitate the puncture of an anatomical wall,
    wherein the insertion device comprises means for detachably connecting to the intracorporeal device, and
    wherein the means for detachably connecting to the intracorporeal device comprises one or more retractable tabs.

2. The system according to claim 1, wherein an inner diameter of the guiding means is smaller than an inner diameter of the outer sheath.

3. The system according to claim 1, wherein the guiding means comprises a substantially rigid material.

4. The system according to claim 1, wherein the guiding means comprises a detection and/or visualisation means.

5. The system according to claim 4, wherein the guiding means comprises a material visible by means of any one of X-ray, fluoroscopy, echocardiography and/or ultrasound techniques.

6. The system according to claim 1, wherein the insertion device further comprises one or more of a dilator and a delivery sheath.

7. The system according to claim 6, further comprising one or more steering means for steering the insertion device.

8. The system according to claim 7, wherein the steering means comprises one or more curved portions on the outer sheath, delivery sheath, dilator and/or guide wire.

9. The system according to claim 7, further comprising a proximal handle for steering the outer sheath, delivery sheath, dilator and/or guide wire.

10. The system according to claim 9, wherein the proximal handle comprises a rotation knob.

11. The system according to claim 1, wherein the insertion device is an all-in-one device further comprising a dilator and a delivery sheath.

12. The system according to claim 1, wherein the insertion device further comprises a dilator, and wherein the dilator is slidable relative to the guide wire.

13. The system according to claim 1, further comprising a delivery sheath and wherein the delivery sheath is slidable relative to the guide wire.

14. The system according to claim 1, wherein the insertion device further comprises a dilator and a delivery sheath, wherein the guide wire, the dilator, and the delivery sheath are movable relative to each other.

15. The system according to claim 1, wherein the insertion device comprises a marker for detecting and/or visualising the position of the transcatheter insertion device.

16. The system according to claim 15, wherein the marker is visible through X-ray, fluoroscopy, echocardiography and/or ultrasound techniques.

17. The system according to claim 15, wherein the insertion device further comprises one or more of a dilator and a delivery sheath, and
wherein the marker is provided on or in the guide wire, dilator, delivery sheath and/or the outer sheath.

18. The system according to claim 1, further comprising a connector, wherein the intracorporeal device is said connector.

19. A transcatheter insertion system for the insertion of an intracorporeal device using an insertion device, comprising:
an insertion device,
an outer sheath arranged and configured to form a passageway for the intracorporeal device and/or the insertion device,
a guiding means for guiding the insertion device, wherein the guiding means is a substantially ring-shaped element having a doughnut shape, and wherein an outer diameter of the doughnut shape of the guiding means fits inside a diameter of the passageway formed by the outer sheath and said guiding means defines an opening which is narrower than a distal opening of the passageway formed by the outer sheath, wherein the guiding means is positioned adjacent to or at a distal end of the outer sheath,
wherein the guiding means comprises an inflatable balloon,
wherein the insertion device further comprises a guide wire,
wherein the guide wire comprises an integrally formed puncture head, and
wherein the puncture head is formed at a distal end of the guide wire and comprises a tapered distal tip, such that the puncture head is configured to facilitate the puncture of an anatomical wall.

20. The system according to claim 19, wherein an inner diameter of the guiding means is smaller than an inner diameter of the outer sheath.

21. The system according to claim 19, wherein the guiding means comprises a substantially rigid material.

22. The system according to claim 19, wherein the guiding means comprises a detection and/or visualisation means.

23. The system according to claim 22, wherein the guiding means comprises a material visible by means of any one of X-ray, fluoroscopy, echocardiography and/or ultrasound techniques.

24. The system according to claim 19, wherein the insertion device further comprises one or more of a dilator and a delivery sheath.

25. The system according to claim 24, further comprising one or more steering means for steering the insertion device.

26. The system according to claim 25, wherein the steering means comprises one or more curved portions on the outer sheath, delivery sheath, dilator and/or guide wire.

27. The system according to claim 25, further comprising a proximal handle for steering the outer sheath, delivery sheath, dilator and/or guide wire.

28. The system according to claim 27, wherein the proximal handle comprises a rotation knob.

29. The system according to claim 19, wherein the insertion device is an all-in-one device further comprising a dilator and a delivery sheath.

30. The system according to claim 19, wherein the insertion device further comprises a dilator, and wherein the dilator is slidable relative to the guide wire.

31. The system according to claim 19, further comprising a delivery sheath and wherein the delivery sheath is slidable relative to the guide wire.

32. The system according to claim 19, wherein the insertion device further comprises: a dilator and a delivery sheath, wherein the guide wire, the dilator, and the delivery sheath are movable relative to each other.

33. The system according to claim 19, wherein the insertion device comprises a marker for detecting and/or visualising the position of the transcatheter insertion device.

34. The system according to claim 33, wherein the marker is visible through X-ray, fluoroscopy, echocardiography and/or ultrasound techniques.

35. The system according to claim 33, wherein the insertion device further comprises one or more of a dilator and a delivery sheath, and
wherein the marker is provided on or in the guide wire, dilator, delivery sheath and/or the outer sheath.

36. The system according to claim 19, wherein the insertion device comprises means for detachably connecting to the intracorporeal device.

37. The system according to claim 36, wherein the means for detachably connecting to the intracorporeal device comprises one or more retractable tabs.

38. The system according to claim 19, further comprising a connector, wherein the intracorporeal device is said connector.

39. The system according to claim 19, further comprising a connector, wherein the intracorporeal device is said connector.

40. A transcatheter insertion system for the insertion of an intracorporeal device using an insertion device, comprising:
   an insertion device,
   an outer sheath arranged and configured to form a passageway for the intracorporeal device and/or the insertion device,
   a guiding means for guiding the insertion device, wherein the guiding means is a substantially ring-shaped element having a doughnut shape, and wherein an outer diameter of the doughnut shape of the guiding means fits inside a diameter of the passageway formed by the outer sheath and said guiding means defines an opening which is narrower than a distal opening of the passageway formed by the outer sheath,
   wherein the guiding means is positioned adjacent to or at a distal end of the outer sheath,
   wherein the guiding means comprises an inflatable balloon,
   wherein the insertion device further comprises a guide wire,
   wherein the guide wire comprises a puncture head, and
   wherein the puncture head is formed at a distal end of the guide wire and comprises a tapered distal tip, such that the puncture head is configured to facilitate the puncture of an anatomical wall.

41. The system according to claim 40, wherein an inner diameter of the guiding means is smaller than an inner diameter of the outer sheath.

42. The system according to claim 40, wherein the guiding means comprises a substantially rigid material.

43. The system according to claim 40, wherein the guiding means comprises a detection and/or visualisation means.

44. The system according to claim 43, wherein the guiding means comprises a material visible by means of any one of X-ray, fluoroscopy, echocardiography and/or ultrasound techniques.

45. The system according to claim 40, wherein the insertion device further comprises one or more of a dilator and a delivery sheath.

46. The system according to claim 45, further comprising one or more steering means for steering the insertion device.

47. The system according to claim 46, wherein the steering means comprises one or more curved portions on the outer sheath, delivery sheath, dilator and/or guide wire.

48. The system according to claim 46, further comprising a proximal handle for steering the outer sheath, delivery sheath, dilator and/or guide wire.

49. The system according to claim 48, wherein the proximal handle comprises a rotation knob.

50. The system according to claim 40, wherein the insertion device is an all-in-one device further comprising a dilator and a delivery sheath.

51. The system according to claim 40, wherein the insertion device further comprises a dilator, and wherein the dilator is slidable relative to the guide wire.

52. The system according to claim 40, further comprising a delivery sheath and wherein the delivery sheath is slidable relative to the guide wire.

53. The system according to claim 40, wherein the insertion device further comprises: a dilator and a delivery sheath, wherein the guide wire, the dilator, and the delivery sheath are movable relative to each other.

54. The system according to claim 40, wherein the insertion device comprises a marker for detecting and/or visualising the position of the transcatheter insertion device.

55. The system according to claim 54, wherein the marker is visible through X-ray, fluoroscopy, echocardiography and/or ultrasound techniques.

56. The system according to claim 54, wherein the insertion device further comprises one or more of a dilator and a delivery sheath, and
   wherein the marker is provided on or in the guide wire, dilator, delivery sheath and/or the outer sheath.

57. The system according to claim 40, wherein the insertion device comprises means for detachably connecting to the intracorporeal device.

58. The system according to claim 57, wherein the means for detachably connecting to the intracorporeal device comprises one or more retractable tabs.

59. The system according to claim 40, further comprising a connector, wherein the intracorporeal device is said connector.

60. The system according to claim 40, further comprising a connector, wherein the intracorporeal device is said connector.

* * * * *